United States Patent [19]

Kim et al.

[11] Patent Number: 5,089,624
[45] Date of Patent: Feb. 18, 1992

[54] DIHYDROPYRIDINE DERIVATIVES

[75] Inventors: Choong S. Kim; Jung J. Suh, both of Seoul; Bong Y. Lee; Chang S. Kim, both of Suwon; Jong W. Lee, Kwacheon; Byung C. Kim, Incheon; Byung H. Han, Seoul, all of Rep. of Korea

[73] Assignee: Yuhan Corporation, Kyonggi-do, Rep. of Korea

[21] Appl. No.: 417,924

[22] Filed: Oct. 6, 1989

[30] Foreign Application Priority Data

Oct. 27, 1988 [KR] Rep. of Korea ............. 14022/1988

[51] Int. Cl.⁵ .......................................... C07D 211/86
[52] U.S. Cl. .................................................. 546/321
[58] Field of Search ........................ 546/321; 514/356

[56] References Cited

U.S. PATENT DOCUMENTS 4,044,141 8/1977 Bossert et al. .................. 546/321
4,600,778 7/1986 Teller et al. .................... 546/321

FOREIGN PATENT DOCUMENTS 1108615 9/1981 Canada .

OTHER PUBLICATIONS

Meyer et al., CA 16038q and CA 16042m, vol. 78, 1973 and CA 95:6997p.
Bossert et al. CA 86:29638a.
Wehinger et al. CA 91:74480g; CA 95: 42922u; CA 99:83613c.
Meyer et al. CA 98:197957v.
Teijin Ltd. CA: 103:12337z.
Nandi et al. CA 109:104796z.

*Primary Examiner*—Jane T. Fan
*Attorney, Agent, or Firm*—Merchant, Gould, Smith, Edell, Welter, & Schmidt

[57] ABSTRACT

The present invention relates to 1,4-dihydropyridine of the formula(I)

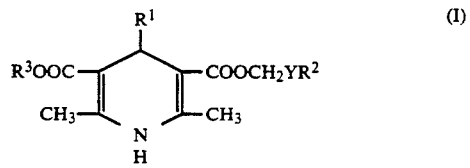

wherein $R^1$ represents a phenyl group which may be substituted by one or two substituents selected from halogeno, nitro, trifluoromethyl and difluoromethoxy group, or 2,1,3-benzoxadiazole-4-yl group, $R^2$ represents a lower alkyl or phenyl group, $R^3$ represents a lower alkyl group and Y represents an oxygen or sulfur atom.

The compounds of the formula(I) can be employed for treatment or prevention of cardiovascular diseases.

3 Claims, No Drawings

DIHYDROPYRIDINE DERIVATIVES

BACKGROUND OF THE INVENTION

1. Field of the Invention

The present invention relates to the novel dihydropyridine, especially 1,4-dihydropyridine having an alkoxymethyl ester or alkylthiomethyl ester group at the 3-position, which is useful as anti-ischaemic and anti-hypertensive agents.

2. Description of the Background

The compound of the formula(I) is much useful as anti-ischaemic and anti-hypertensive agents.

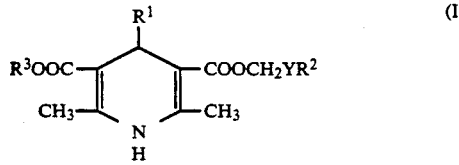

wherein $R^1$ represents a phenyl group, which may be substituted by one or two substitutents selected from halogeno, nitro, trifluoro methyl and difluoromethoxy group, or 2,1,3-benzoxadiazole-4-yl group, $R^2$ represents a lower alkyl or phenyl group, $R^3$ represents a lower alkyl group and Y represents an oxygen or sulfur atom.

The term "aryl" as used in this specification includes, for example, phenyl which may be substituted by one or two substitutents selected from halogeno, nitro, trifluoromethyl and difluoromethoxy group. "Halogeno" means fluoro, chloro, bromo or iodo.

The term "lower" used in connection with an alkyl group is intended to mean the one having 1 to 4 carbon atom. "Lower Alkyl" may be ones having a straight or branched and saturated hydrocarbon chain such as methyl, ethyl, propyl, isopropyl, butyl, isobutyl or t-butyl.

It is disclosed that the compounds substituted by alkoxyethyl ester and alkylthioethyl ester group at the 3-position reduce the intracellular movement of calcium ion and have an ability to reduce the blood pressure(cf. Spanish Laid Open Publication No. 537,427 and Ger. Offenlegungsschrift DE 2,747,513, Al).

The 1,4-dihydropyridine derivatives described above when used in anti-ischaemic and anti-hypertensive agents are not completely satisfactory as an excellent anti-ischaemic and anti-hypertensive agents.

Therefore, the development of an anti-ischaemic and anti-hypertensive agents possessing stability as well as an excellent effect has been desired.

In view of such circumstances, the inventors of the present invention synthesized a number of compounds and examined their pharmacological effects. As a result of these investigations, it was found that the 1,4-dihydropyridine derivative substituted by alkoxymethyl ester or alkylthiomethyl ester group at the 3-position shown by the following formula(I) fulfilled the above conditions and possessed an excellent anti-ischaemic and anti-hypertensive effect.

SUMMARY OF THE INVENTION

Accordingly, an object of the present invention is to provide a 1,4-dihydropyridine derivative of the following formula(I),

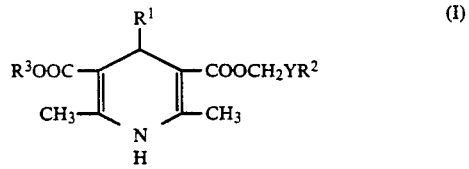

wherein $R^1$ represents a phenyl group, which may be substituted by one or two substitutents selected from halogeno, nitro, trifluoromethyl and difluoromethyl group, or 2,1,3-benzoxadiazole-4-yl group, $R^2$ represents a lower alkyl or phenyl group, $R^3$ represents a lower alkyl group and Y represents an oxygen or sulfur atom.

Other object of the present invention is to provide an anti-ischaemic and anti-hypertensive agent comprising, as an active ingredient, a 1,4-dihydropyridine derivative of the above formula(I).

The further objects, features and advantages of the invention will hereinafter become more readily apparent from the following description.

DETAILED DESCRIPTION OF THE INVENTION AND PREFERRED EMBODIMENTS

The compound of the present invention can be prepared by the esterification reaction from the corresponding dihydropyridine monocarboxylic acids and either alkylthiomethyl halides or alkoxymethyl halides, according to the following reaction formula,

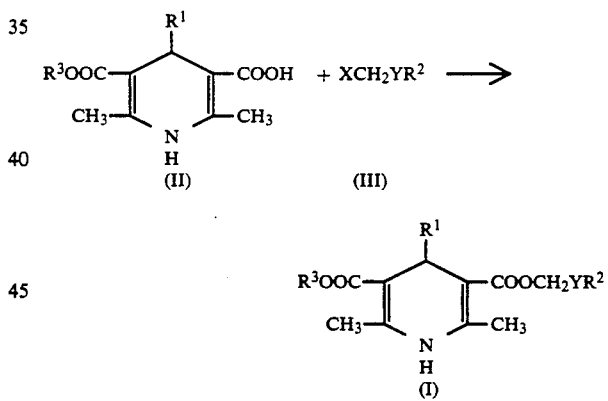

wherein X represents a halogen atom, and $R^1$, $R^2$, $R^3$ and Y are as defined above.

This method is carried out by adding the acid acceptor to a suspension of the compound(II) in a appropriate organic solvent to afford a clear solution, and then to the reaction mixture alkylthiomethyl or alkoxymethyl halide of the formula(III) is added. And the reaction mixture was stirring for 2-8 hours at room temperature or if required, with heating. The reaction of the invention is preferably proceeded in the solvent which does not severely affect the reaction. Here, as the solvent, there may be employed acetonitrile, tetrahydrofuran, dimethylformamide, etc. However, the solvent is not restricted to such specific examples. If necessary, the above method can be carried out under the catalyst such as sodium iodide.

The starting material of the formula(II is available commercially or can be prepared by the similar methods to those of the prior art such as Japanese Laid Open Publication No. 55-64570.

As the preferred acid acceptors in the above reaction, there may be employed triethylamine, potassium carbonate, etc.

Hereinafter are presented experimental examples to illustrate the anti-ischaemic and anti-hypertensive effects o compound(I) of the present invention. These examples are given for illustration of the invention and are not intended to be limiting thereof.

EXPERIMENTAL EXAMPLES

Test Method

The test is performed by mounting spiral strips of rabbit aorta with one end fixed and the other attached to a force transducer. The mounted tissue is immersed in a physiological salt solution containing potassium ion at a concentration of 35 millimole and no calcium. Calcium chloride is added to the bath to give a final calcium ion concentration of 2 millimole. The change in tension caused by the resulting contraction of the tissue is noted. The bath is drained and replaced with fresh salt solution and, 45 minutes later the test is repeated with the addition of the compound being tested in the presence of salt solution and, 45 minutes later the test is repeated with the addition of the compound being tested in the presence of salt solution. The concentration of compound required to reduce the response by 50% is recorded. The anti-hypertensive activity of the compounds is also evaluated oral administration by measuring the decrease fall in blood pressure in spontaneously hypertensive rats.

Test Results

The molar concentration of the compounds required to reduce the response by 50% in the test, i.e. IC , is given in Table 1.

The smaller the concentration, the more active the compound, i.e. the most active compound is the product of Example 1.

TABLE 1

| compound | $IC_{50}$ ($10^{-8}$ M) | compound | $IC_{50}$ ($10^{-8}$ M) |
| --- | --- | --- | --- |
| Example 1 | 0.4 | Example 8 | 2.6 |
| Example 2 | 2.0 | Example 9 | 2.9 |
| Example 3 | 5.6 | Example 10 | 2.0 |
| Example 4 | 1.7 | Example 11 | 8.0 |
| Example 5 | 2.9 | Example 12 | 1.1 |
| Example 6 | 1.9 | Example 13 | 14.2 |
| Example 7 | 4.2 | control* | 3.5 |

*control: Nicardipine

The compound of the formula(I) of the present invention has a highly potential pharmacological action with marked long duration against cardiovascular diseases such as hypertension, angina pectoris, coronary artery thrombosis, myocardial infarction and cerebral blood flow disturbance. Accordingly, the compound of formula(I) of the invention are useful as remedies such as an anti-hypertensive agent, cerebral vasodilator, anti-stenocardiac agent, anti-cardiac infarction remedy and anti-arrhythmic agent, etc.

Accordingly, the present invention also provides a pharmaceutical composition which comprises the 1,4-dihydropyridine derivative of formula(I) as active ingredient with a pharmaceutically acceptable carrier, for preventing or treating the cardiovascular diseases. The compound of formula(I) of the invention is useful for preparing such a pharmaceutical composition not only due to its marked efficacy in curing and preventing hypertension, cerebral blood flow disturbance, stenocardiac. etc. but also due to its chemical stability, and resulting easiness of being prepared into various dosage forms. The compounds of formula(I) of the invention can be administered by oral, rectal and parenteral routes such as intravenous, subcutaneous and intramuscular administration.

When the compound of the formula(I) is used as the remedies the dose is different depending upon the administration route, the symptoms, age and sex of the patient. However, in the case of oral administration in normal adults, a daily administration of of 0.06–10 mg/kg/day once or over several doses is desirable, while for non-oral administration, the daily dose range is 0.006–1 mg/kg/day, also either given as a single dose or over several doses.

For oral administration forms such as tablets, pills, granules, powders, suspensions, capsules and the like can be used. They can be prepared by commonly known methods. In other words, tablets, pills, granules, powders, suspensions or capsules can be prepared by formulating appropriate combinations of compound(I) and excipients such as lactose, starch or the like, binders such as carboxymethyl cellulose, methyl cellulose, polyvinyl pyrrolidine or the like, disintegrators such as crystalline cellulose, sodium alginate, sodium bicarbonate, sodium lauryl sulfate or the like, and lubricants such as talc, magnesium stearate, or the like.

Solutions and suspensions can be prepared by the ordinary skill in the art, using glycerol esters such as tricaprylin, triacetin, etc. and alcohols such as ethanol, etc.

The dosage forms for subcutaneous, intramuscular and intravenous administration are prepared in the form of an aqueous or non-aqueous solution.

In the preparation of an aqueous solutions, an isotonic sodium chloride solution or a buffer solution is used. In the preparation of non-aqueous solutions, propylene glycol, olive oil or ethyl oleate, etc., is used and, if required, antiseptics or stabilizers may be added.

Injections ca be sterilized by filtration through the membrane filter or by combination of disinfectants with other adjuvants.

The dosage forms for percutaneous administration are ointments and creams. Ointments can be prepared by commonly known methods using fatty oils such as castor oil, olive oil and vaseline, and creams are prepared by using fatty oils and emulsifying agents such as diethylene glycol, sorbitan monofatty acid ester, etc.

For rectal administration, ordinary suppositories in the form of soft gelatin capsules are used.

Other features of the invention will become apparent in the course of the following description of the exemplary embodiments which are given for illustration of the invention and are not intended to be limiting there of.

EXAMPLES

Example 1

Preparation of
2,6-dimethyl-4-(3'-nitrophenyl)-1,4-dihydropyridine-3,5-dicarboxylic acid 3-methylthiomethyl ester 5-methyl ester A solution of 2,6-dimethyl-4-(3'-nitrophenyl)-1,4-dihydro pyridine-3,5-dicarboxylic acid 5-methyl ester(3.32g), triethylamine(2.5ml)and chloromethyl methyl sulfide(0.9ml) in 30ml of acetonitrile was heated at 65° C. for 3 hours. The solvent was removed in vacuum, and then the residue was dissolved in ethylacetate. The ethylacetate solution was washed with water and dried over anhydrous sodium sulfate and the solvent was evaporated under reduced pressure. The oily residue was purified by silica gel column chromatography (ethylacetate:n-hexane=1:3). The eluent was concentrated in vacuum to afford a yellow solid which was recrystallized from methyl alcohol to give the titled compound(1.2g):

m.p. 128°-130° C.,
$^1$H NMR(CDCl$_3$) ; 2.3(s, 3H), 2.4(s, 6H), 3.7(s, 2H), 6.4s, 1H), 7.1-8.6(m, 4H)
IR(KBr) cm$^{-1}$; 3323(NH), 1701(C=O).

Example 2-12

The following compounds were prepared by the similar method described in Example 1 and characterized in the form indicated, starting from the appropriate 1,4-dihydropyridine-3,5-dicarboxylate monoester.

(3.32 g), potassium carbonate(0.7 g), potassium iodide(1.7 g) and chloromethyl phenyl sulfide(1.34 ml) in 30 ml of dimethylformamide was stirred for 12 hours at room temperature. The reaction mixture was diluted with water and then extracted with dichloromethane. Organic layer was subsequently washed with brine, aqueous sodium hydroxide solution and water, and then dried over anhydrous sodium sulfate. The solvent was evaporated in vacuum. The residue was dissolved in ethyl alcohol to give 3.5 g. of yellow crystals:

m.p. 155°-157° C.,
$^1$H-NMR(CDCl$_3$) ; 2.4(s, 6H), 3.7(s, 3H), 5.1(s, 1H), 5.4(s, 2H), 6.2(s, 1H), 7.2-8.0(m, 9H)
IR(KBr) cm$^{-1}$; 3337(NH), 1707(C=O).

FORMULATION EXAMPLES

Example 14 (Tablets)

Tablets were prepared using known procedures and the following ingredients. These tablets can be prepared into film coated or sugar coated tablets.

| Ex. No. | R$^1$ | R$^2$ | R$^3$ | Y | m.p. (°C.) | H$^1$NMR(CDCl) | IR (KBr: cm$^{-1}$) |
|---|---|---|---|---|---|---|---|
| 2. | 3-nitrophenyl | Me | Et | S | 138-140 | 1.2(T, 3H), 2.0(s, 3H), 2.3(d, 6H), 4.1(q, 2H), 5.1(s, 1H+2H), 6.2(s, 1H), 7.6-8.2(m, 4H) | 3326(NH) 1696(C=O) |
| 3. | 3-nitrophenyl | Me | i-Pr | S | | 1.0-1.5(d, 6H), 2.1 (s, 3H), 2.4(s, 6H), 5.1(m, 4H), 6.0(s, 1H), 1H), 7.2-8.3(m, 4H) | 3345(NH) 1699(C=O) |
| 4. | 3-nitrophenyl | Et | Me | S | 116- | 1.2(t, 3H), 2.2-2.8 118(m, 8H), 3.7(s, 3H), 5.2(s, 1H+2H), 6.5 | 3341(NH), 1704, 1654 (C=O) |
| 5. | 2,3-dichlorophenyl | Me | Me | S | 165-166 | 2.1(s, 3H), 2.3(d, 6H), 3.6(s, 3H), 5.1(s 2H), 5.5(s, 1H), 5.8(s, 1H), 6.9-7.5(m, 3H) | 3337(NH), 1701, 1661(C=O) |
| 6. | 2-trifluoromethylphenyl | Me | Me | S | 104-107 | 2.1(s, 3H), 2.4(d, 6H), 3.7(s, 3H), 4.9-5.1 (d+d, 2H), 5.6(s, 1H), 5.9(s, 1H), 7.2-7.7 (m, 4H) | 3319(NH), 1703, 1677(C=O) |
| 7. | 3-nitrophenyl | Me | Me | O | 133-134 | 2.4(d, 6H), 3.4(s, 3H), 3.7(s, 3H), 5.2(m, 2H), 6.4(s, 1H), 7.2-8.2 (m, 4H) | 3340(NH), 1707, 1654(C=O) |
| 8. | 3-nitrophenyl | Me | i-Pr | O | 126-128 | 1.3(q, 6H), 2.4(d, 6H), 3.4(s, 3H), 5.2(m, 4H), 6.1(s, 1H), 7.2-8.2 (m, 4H) | 3340(NH), 1651, 1699(C=O) |
| 9. | 3-nitrophenyl | Et | Me | O | 115-116 | 1.2(t, 3H), 2.4(d, 6H), 3.5(q, 2H), 5.2(m, 2H), 6.2(s, 1H), 7.2-8.4 (m, 4H) | 3329(NH), 1710(C=O) |
| 10. | 2,3-dichlorophenyl | Me | Me | O | 130-131 | 2.3(d, 6H), 3.2(s, 3H), 3.6(s, 3H), 5.0-5.5 (q, 2H), 5.5(s, 1H), 6.0(s, 1H), 6.9-7.5 | 3329(NH), 1701, 1666(C=O) |
| 11. | 2,1,3-benzoxadiazole-4-yl | Me | Me | S | 121-123 | 2.0(s, 3H), 2.4(d, 6H), 3.6(s, 3H), 5.1(s, 2H), 5.5(s, 1H), 6.5(s, 1H), 7.2-7.7(m, 3H) | 3300(NH) 1699, 1646(C=O) |
| 12. | 2-nitrophenyl | Me | Me | S | 63-73 | 2.0(s, 3H), 2.3(d, 6H), 3.5(s, 3H), 5.0(dd, 2H), 5.6(s, 1H), 7.3-7.8 (m, 4H), 9.1(s, 1H) | 3484(NH), 1670(C=O) |

Example 13

Preparation of 2,6-dimethyl-4-(3-nitrophenyl)-1,4-dihydropyridine-3,5-dicarboxylic acid 3-phenylthiomethyl, 5-methylester A solution of 2,6-dimethyl-4-(3-nitrophenyl)-1,4-dihydropyridine-3,5-dicarboxylic acid 5-methyl ester

| Compound No. 1* | 5.0 mg |
|---|---|
| Lactose | 50.0 mg |
| Corn starch | 25.0 mg |
| Crystalline Cellulose | 25.0 mg |
| Methyl Cellulose | 1.5 mg |

|                    |              |
|--------------------|--------------|
| Magnesium stearate | 1.0 mg       |
| Total              | 107.5 mg/tablet |

*Compound No. 1: 2,6-dimethyl-4-(3'-nitrophenyl)-1,4-dihydropyridine-3,5-dicarboxylic acid 3-methylthiomethyl ester 5-methyl ester

Example 15 (Capsules)

Granules were prepared using known procedures and the following ingredients, and then filled into No. 1 capsules.

|                    |              |
|--------------------|--------------|
| Compound No. 1     | 10 mg        |
| Lactose            | 80 mg        |
| Starch             | 30 mg        |
| Talc               | 5 mg         |
| Magnesium stearate | 1 mg         |
| Total              | 126 mg/capsule |

Example 16 (injections)

Injection was prepared according to known procedures and the following ingredients.

|                              |         |
|------------------------------|---------|
| Compound No. 1               | 4 g     |
| Polyethylene glycol 4000     | 0.9 g   |
| Sodium chloride              | 0.9 g   |
| Polyoxyethylene sorbitan monooleate | 0.4 g |
| p-hydroxy methylbenzoate     | 0.18 g  |
| p-hydroxy propylbenzoate     | 0.02 g  |
| sterilized water             | 100 ml  |

Obviously, numerous modification and variations of the present invention are possible in the light of the above teachings. It is therefore to be understood that within the scope of the appended claims, the invention may be practiced otherwise than as specifically described herein.

What is claimed is:

1. A dihydropyridine compound of the formula (I),

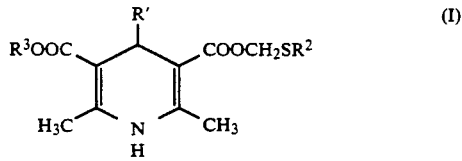

wherein $R^1$ represents 2,3-dichlorophenyl, difluoromethyoxyphenyl, or 2,1,3-benzoxadiazole-4-yl, $R^2$ represents a lower alkyl group, and $R^3$ represents a lower alkyl group.

2. A dihydropyridine compound of the formula (I),

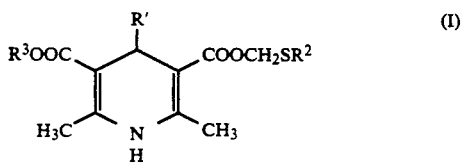

wherein $R^1$ represents a 2-nitrophenyl or 2-trifluoromethylphenyl group, $R^2$ represents a lower alkyl group, and $R^3$ represents a methyl group.

3. A dihydropyridine compound of the formula (I),

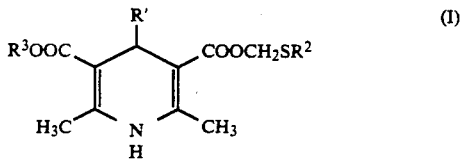

wherein $R^1$ represents a 3-nitrophenyl group, $R^2$ represents a lower alkyl group, and $R^3$ represents a methyl, ethyl or isopropyl group.

* * * * *